(12) United States Patent
Chiba

(10) Patent No.: US 9,183,427 B2
(45) Date of Patent: Nov. 10, 2015

(54) DIAGNOSTIC SYSTEM

(75) Inventor: Toru Chiba, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 14/240,116

(22) PCT Filed: Aug. 28, 2012

(86) PCT No.: PCT/JP2012/071658
§ 371 (c)(1),
(2), (4) Date: Feb. 21, 2014

(87) PCT Pub. No.: WO2013/047054
PCT Pub. Date: Apr. 4, 2013

(65) Prior Publication Data
US 2014/0185907 A1 Jul. 3, 2014

(30) Foreign Application Priority Data

Sep. 29, 2011 (JP) .................................. 2011-213623

(51) Int. Cl.
| | |
|---|---|
| *G06K 9/00* | (2006.01) |
| *A61B 1/00* | (2006.01) |
| *A61B 1/06* | (2006.01) |
| *A61B 8/08* | (2006.01) |

(52) U.S. Cl.
CPC .......... *G06K 9/0014* (2013.01); *A61B 1/00009* (2013.01); *A61B 1/0638* (2013.01); *A61B 1/0646* (2013.01); *A61B 8/48* (2013.01)

(58) Field of Classification Search
USPC ......................................................... 382/134
See application file for complete search history.

(56) References Cited

U.S. PATENT DOCUMENTS

| | | | |
|---|---|---|---|
| 4,959,710 A | 9/1990 | Uehara et al. | |
| 5,983,120 A * | 11/1999 | Groner et al. | 600/310 |
| 6,678,398 B2 * | 1/2004 | Wolters et al. | 382/128 |
| 8,411,989 B2 | 4/2013 | Chiba | |

(Continued)

FOREIGN PATENT DOCUMENTS

| | | |
|---|---|---|
| CN | 102188226 | 9/2011 |
| JP | 6-315477 | 11/1994 |

(Continued)

OTHER PUBLICATIONS

Office Action issued in China Counterpart Patent Appl. No. 201280046407.7, dated Sep. 2, 2015, along with an English translation thereof.

*Primary Examiner* — Yon Couso
(74) *Attorney, Agent, or Firm* — Greenblum & Bernstein P.L.C.

(57) ABSTRACT

A diagnostic system comprises a spectral image pickup means that picks up a spectral image in a predetermined wavelength region in a body cavity and obtains spectral image data, an image processing means that obtains, from the spectral image data, an index-value for discriminating between a diseased portion and a healthy portion, and generates and outputs an indicator image based on the index-value, and a monitor on which the indicator image is displayed, wherein, for each pixel of the spectral image, the image processing means defines β obtained by a predetermined expression as the index-value, while using the spectral image data $P_1$ at a first wavelength which is around a wavelength of 542 nm, the spectral image data $P_2$ at a second wavelength which is around a wavelength of 558 nm and the spectral image data $P_3$ at a third wavelength which is around a wavelength of 578 nm.

16 Claims, 8 Drawing Sheets

(56) References Cited

U.S. PATENT DOCUMENTS

| | | |
|---|---|---|
| 8,657,737 B2 | 2/2014 | Saito |
| 2007/0024946 A1* | 2/2007 | Panasyuk et al. ............. 359/253 |
| 2007/0232930 A1* | 10/2007 | Freeman et al. ............. 600/476 |
| 2010/0054576 A1* | 3/2010 | Tsujita ......................... 382/134 |
| 2012/0191365 A1 | 7/2012 | Chiba |
| 2013/0197371 A1 | 8/2013 | Chiba et al. |
| 2014/0010424 A1 | 1/2014 | Chiba et al. |

FOREIGN PATENT DOCUMENTS

| | | |
|---|---|---|
| JP | 2003-164416 | 6/2003 |
| JP | 2004-219092 | 8/2004 |
| JP | 2007-135989 | 6/2007 |
| JP | 2009-66301 | 4/2009 |
| JP | 2010-268838 | 12/2010 |
| WO | 2004/063683 | 7/2004 |

\* cited by examiner

DIAGNOSTIC SYSTEM

TECHNICAL FIELD

The present invention relates to a diagnostic system configured to display an image of a region that is highly likely to be a diseased portion in a living tissue.

BACKGROUND ART

Recently, an electronic endoscope having a function as a spectrometer has been proposed as described, for example, in Japanese Patent Provisional Publication No. JP2007-135989A. By using such an electronic endoscope, it is possible to obtain the spectral property (the distribution of light absorption property for each frequency) of a living tissue such as a mucous membrane of a digestive organ, e.g., a stomach or a rectum. It is known that the spectral property of a substance reflects information concerning the types or densities of components contained in the vicinity of a surface layer of a living tissue being an observation target, which is established in a field belonging to academic frameworks of analytical chemistry. It is also known in this field that the spectral property of a substance consisting of a composite is information obtained by superimposing the spectral properties of essential components constituting the composite.

A diseased portion in a living tissue may contain a substance having a chemical configuration that is rarely contained in a healthy living tissue. Therefore, a spectral property of a living tissue containing a diseased portion is different from a spectral property of a living tissue containing only a healthy portion. Since the spectral properties of the healthy portion and the diseased portion are different from each other as described above, it becomes possible to judge whether or not a living tissue contains a diseased portion by comparing the spectral property of the healthy portion with that of the diseased portion.

SUMMARY OF THE INVENTION

As described above, researches have been carried out to determine the presence of a diseased portion in a living tissue by obtaining spectral information from living bodies and by using the differences of spectral properties obtained from the spectral information. However, the known researches have not proposed any practical diagnostic methods to generate images for determining where in the living tissue there is a change in the spectral property caused by diseased portions, and identify the position and the extent of a diseased portion while comparing the diseased portion with the surrounding tissues.

The present invention is made to solve the above described problem. That is, the object of the invention is to provide a diagnostic system capable of displaying an image enabling an operator to easily discriminate between a healthy portion and a diseased portion.

To achieve the above described object, a diagnostic system according to the invention comprises: a spectral image pickup means that picks up a spectral image in a predetermined wavelength region in a body cavity and obtains spectral image data; an image processing means that obtains, from the spectral image data, an index-value for discriminating between a diseased portion and a healthy portion, and generates and outputs an indicator image based on the index-value; and a monitor on which the indicator image is displayed. For each pixel of the spectral image, the image processing means defines $\beta$ obtained by a following expression as the index-value, $$\beta = 2P_2 - P_1 - P_3 \qquad \text{(EXPRESSION 1)}$$

while using the spectral image data $P_1$ at a first wavelength which is around a wavelength of 542 nm, the spectral image data $P_2$ at a second wavelength which is around a wavelength of 558 nm and the spectral image data $P_3$ at a third wavelength which is around a wavelength of 578 nm.

It has been reported that there is a case where, in a blood flow component of a living body, a diseased portion and a healthy portion have different component ratios of oxyhemoglobin and deoxyhemoglobin and such a difference can be advantageously used for detecting disease or estimating progress of disease. It is also known that the light absorption properties of oxyhemoglobin and deoxyhemoglobin are different from each other. The invention was made by focusing on this point. According to the above described configuration, the indicator image based on the index-value $\beta$ indicating the component ratio between oxyhemoglobin and deoxyhemoglobin is displayed. Therefore, an operator is able to easily discriminate between a healthy portion and a diseased portion.

The image processing means may obtain a ratio between oxyhemoglobin and deoxyhemoglobin from the index-value, and generate the indicator image based on the ratio. In this case, it is preferable that the image processing means generates the indicator image by assigning a predetermined color based on the ratio between oxyhemoglobin and deoxyhemoglobin to each pixel of the spectral image. According to such a configuration, it becomes possible to further easily and precisely discriminate between a healthy portion and a diseased portion.

It is preferable that the image processing means outputs a color image by combining the spectral image data in wavelength bands corresponding to blue, green and red, and that the color image and the indicator image are displayed on the monitor while being aligned side by side. According to such a configuration, since it becomes possible to easily identify a diseased portion by making a comparison between the color image and the indicator image being observed, it also becomes possible to easily check and specify an area required for excision and the like in a surgical operation.

The diagnostic system may include a standardizing means that integrates the spectral image data in a predetermined wavelength range to obtain an integrated value, and corrects the spectral image data so that the integrated value coincides with a reference value. In this case, it is preferable that the predetermined wavelength range is selected from a range of 600 nm to 800 nm. According to such a configuration, since it is possible to correct the fluctuations in a light amount due to a reflection angle difference between the pixels constituting the spectral image, it is possible to provide an indicator image which enables further precisely discriminating between a healthy portion and a diseased portion.

The diagnostic system may further include a standardizing means that corrects the spectral image data so that the spectral image data at a wavelength corresponding to an isosbestic point of hemoglobin coincides with a reference value.

It is preferable that the predetermined wavelength region is 400 nm to 800 nm, and that the spectral image includes a plurality of images shot at an interval of a predetermined wavelength defined in a range of 1 nm to 10 nm.

The first wavelength may be a certain wavelength in a range of 530 nm to 545 nm, the second wavelength may be a certain wavelength in a range of 550 nm to 568 nm, and the third wavelength may be a certain wavelength in a range of 570 nm to 584 nm.

According to another aspect, a diagnostic system according to the invention comprises: a spectral image pickup means that picks up a spectral image in a predetermined wavelength region in a body cavity and obtains spectral image data; an image processing means that obtains, from the spectral image data, an index-value for discriminating between a diseased portion and a healthy portion, and generates and outputs an indicator image based on the index-value; and a monitor on which the indicator image is displayed. For each pixel of the spectral image, the image processing means defines γ obtained by a following expression as the index-value, $$\gamma = \frac{2P_2 - P_1 - P_3}{a} \qquad \text{(EXPRESSION 2)}$$

while using the spectral image data $P_1$ at a wavelength which is around a wavelength of 542 nm, the spectral image data $P_2$ at a wavelength which is around a wavelength of 558 nm, the spectral image data $P_3$ at a wavelength which is around a wavelength of 578 nm and a standardization coefficient a indicating an amount of light incident on each pixel.

As described above, according to the diagnostic system of the invention, an image which enables easily discriminating between a diseased portion and a healthy portion can be displayed. Therefore, a time for a diagnosis can be shortened and it becomes possible to easily check and specify an area required for excision and the like in a surgical operation.

BRIEF DESCRIPTION OF THE DRAWINGS

FIG. 2A is a graph showing a spectrum of a pixel corresponding to a diseased portion of the gastric mucosa, and FIG. 2B is a graph showing a spectrum of a pixel corresponding to a healthy portion of the gastric mucosa.

EMBODIMENTS FOR CARRYING OUT THE INVENTION

In the following, an embodiment according to the invention is described with reference to the accompanying drawings.

Figure 1:
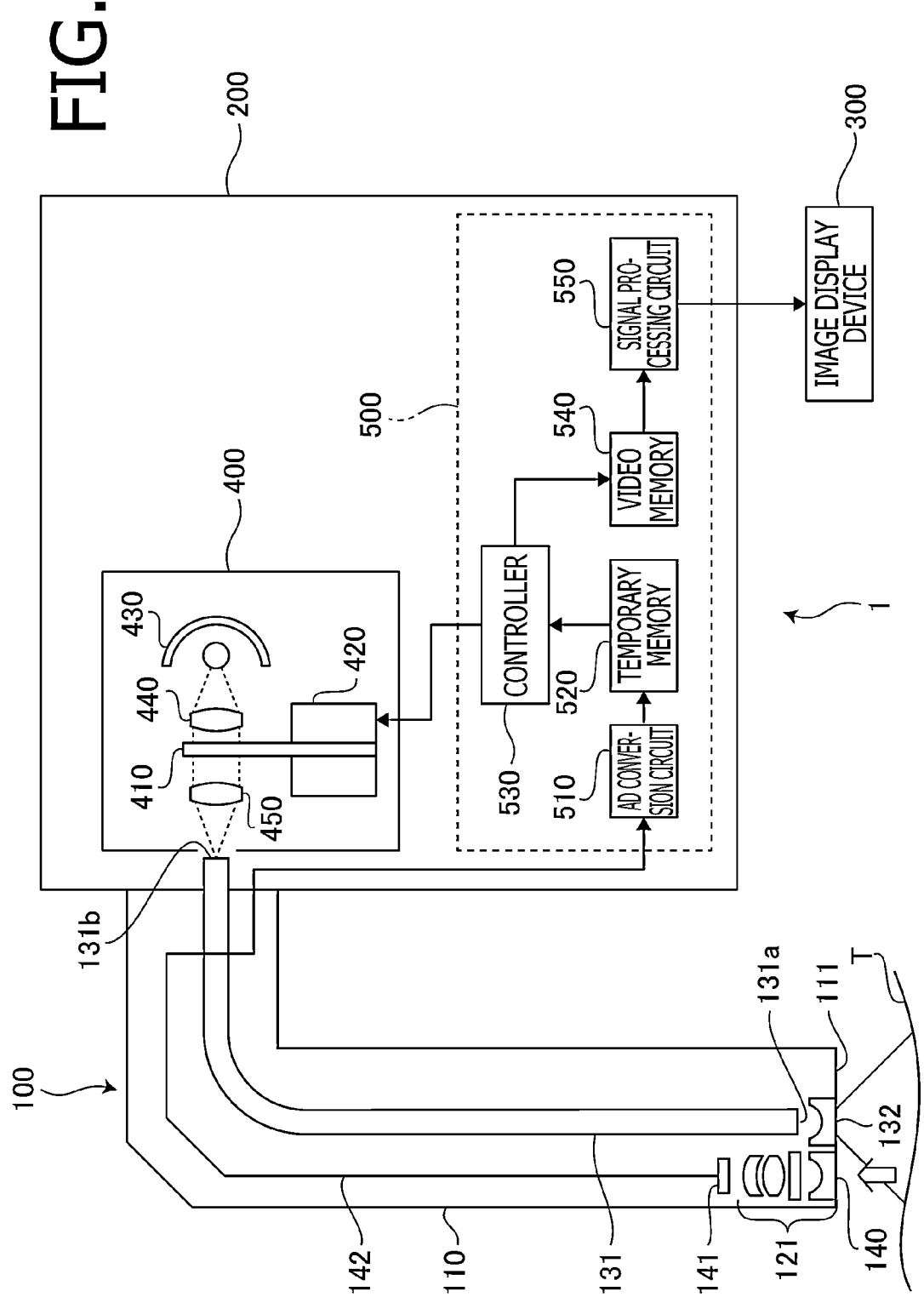
FIG. 1 is a block diagram illustrating a diagnostic system according to an embodiment of the invention.

FIG. 1 is a block diagram of a diagnostic system 1 according to the embodiment of the invention. The diagnostic system 1 according to the embodiment is configured to generate an indicator image to be referred to by a medical doctor for diagnosing a disease of a digestive organ, such as a stomach or a rectum. The diagnostic system 1 includes an electronic endoscope 100, a processor 200 for an electronic endoscope and an image display device 300. In the processor 200 for an electronic endoscope, a light source unit 400 and an image processing unit 500 are accommodated.

The electronic endoscope 100 includes an insertion tube 110 to be inserted into a body cavity, and an objective optical system 121 is provided at a tip portion (an insertion tube tip portion) 111 of the insertion tube 110. An image of a living tissue T around the insertion tube tip portion 111 is formed by the objective optical system 121 on a light-receiving surface of an image pick-up device 141 accommodated in the insertion tube tip portion 111. As the image pick-up device 141, for example, a CCD (Charge Coupled Device) image sensor having a three primary color filter on the front side thereof is used.

The image pick-up device 141 periodically (e.g., at intervals of 1/30 seconds) outputs an image signal corresponding to the image formed on the light-receiving surface. The image signal outputted by the image pick-up device 141 is transmitted to the image processing unit 500 of the processor 200 for an electronic endoscope via a cable 142.

The image processing unit 500 includes an AD conversion circuit 510, a temporary memory 520, a controller 530, a video memory 540 and a signal processing circuit 550. The AD conversion circuit 510 executes the AD conversion for the image signal transmitted from the image pick-up device 141 of the electronic endoscope 100 via the cable 142 to output digital image data. The digital image data outputted from the AD conversion circuit 510 is transmitted to and stored in the temporary memory 520. The controller 530 processes a piece of or a plurality of pieces of image data stored in the temporary memory 520 to generate one piece of display image data, and transmits the display image data to the video memory 540. For example, the controller 530 produces the display image data generated from a piece of image data, the display image data in which a plurality of pieces of image data are arranged and displayed, or the display image data in which an image obtained by subjecting a plurality of pieces of image data to an image operation and a graph obtained as a result of the image operation are displayed, and stores them in the video memory 540. The signal processing circuit 550 converts the display image data stored in the video memory 540 into a video signal having a predetermined format (e.g., an NTSC format), and outputs the video signal. The video signal outputted from the signal processing circuit 550 is inputted to the image display device 300. As a result, an endoscopic image shot by the electronic endoscope 100 is displayed on the image display device 300.

A light guide 131 is provided in the electronic endoscope 100. A tip portion 131a of the light guide 131 is disposed close to the insertion tube tip portion 111, and a proximal end portion 131b of the light guide 131 is connected to the processor 200 for an electronic endoscope. The processor 200 for an electronic endoscope includes therein the light source unit 400 (described later) having a light source 430 generating a large amount of white light, e.g., a Xenon lamp. Light generated by the light source unit 400 is incident on the proximal end portion 131b of the light guide 131. The light which has entered into the proximal end portion 131b of the light guide 131 is guided to the tip portion 131a through the light guide 131, and is emitted from the tip portion 131a. In the vicinity of the tip portion 131a of the light guide 131 in the insertion tube tip portion 111 of the electronic endoscope 100, a lens 132 is provided. The light emitted from the tip portion 131a of the light guide 131 passes through the lens 132, and illuminates the living tissue T near the insertion tube tip portion 111.

As described above, the processor 200 for an electronic endoscope has both the function as a video processor which processes the image signal outputted from the image pick-up device 141 of the electronic endoscope 100, and the function as a light source device which supplies illumination light for illuminating the living tissue T near the insertion tube tip portion 111 of the electronic endoscope 100 to the light guide 131 of the electronic endoscope 100.

In this embodiment, the light source unit 400 of the processor 200 for an electronic endoscope includes the light source 430, a collimator lens 440, a spectral filter 410, a filter control unit 420 and a condenser lens 450. The white light emitted from the light source 430 is converted by the collimator lens 440 into a collimated beam, passes through the spectral filter 410, and then is incident on the proximal end portion 131b of the light guide 131 through the condenser lens 450. The spectral filter 410 is a filer of a circular plate type which breaks down the white light from the light source 430 into light of a predetermined wavelength (i.e., selects a wavelength), and selects and outputs light of a narrow band of 400 nm, 405 nm, 410 nm, . . . , 800 nm (a bandwidth of approximately 5 nm) depending on a rotation angle thereof. The rotation angle of the spectral filter 410 is controlled by the filter control unit 420 connected to the controller 530. Since the controller 530 controls the rotation angle of the spectral filter 410 via the filter control unit 420, the light of a predetermined wavelength is incident on the proximal end portion 131b of the light guide 131, and the living tissue T near the insertion tube tip portion 111 is illuminated. Then, light reflected from the living tissue T is converged onto the light-receiving surface of the image pick-up device 141 as described above, and the image signal is transmitted to the image processing unit 500 via the cable 142.

The image processing unit 500 is configured as a device which obtains a plurality of spectral images at intervals of a wavelength of 5 nm from the image signal of the living tissue T inputted via the cable 142. Specifically, the image processing unit 500 captures the spectral images of the respective wavelengths when the spectral filter 410 selects and outputs the narrow band light (a bandwidth of approximately 5 nm) having the center wavelengths of 400 nm, 405 nm, 410 nm, . . . , 800 nm, and stores the intensity values (intensity information) in the temporary memory 520 as the spectral image data.

The image processing unit 500 has the function of processing the spectral image data stored for each wavelength of the spectral filter 410, and generating a color image or an indicator image, as described later. Then, the image processing unit 500 controls the image display device 300 to display the processed color image and the indicator image.

It should be noted that, as the spectral filter 410, a Fabry-Perot filter or a filter using a transmission type diffraction grating can be used, for example.

As described above, the image processing unit 500 according to the embodiment has the function of generating an indicator image enabling an operator to easily discriminate between a diseased portion and a healthy portion, by using a plurality of spectral images of different wavelengths. In the following, the function of generating an indicator image is explained.

Figure 2A:
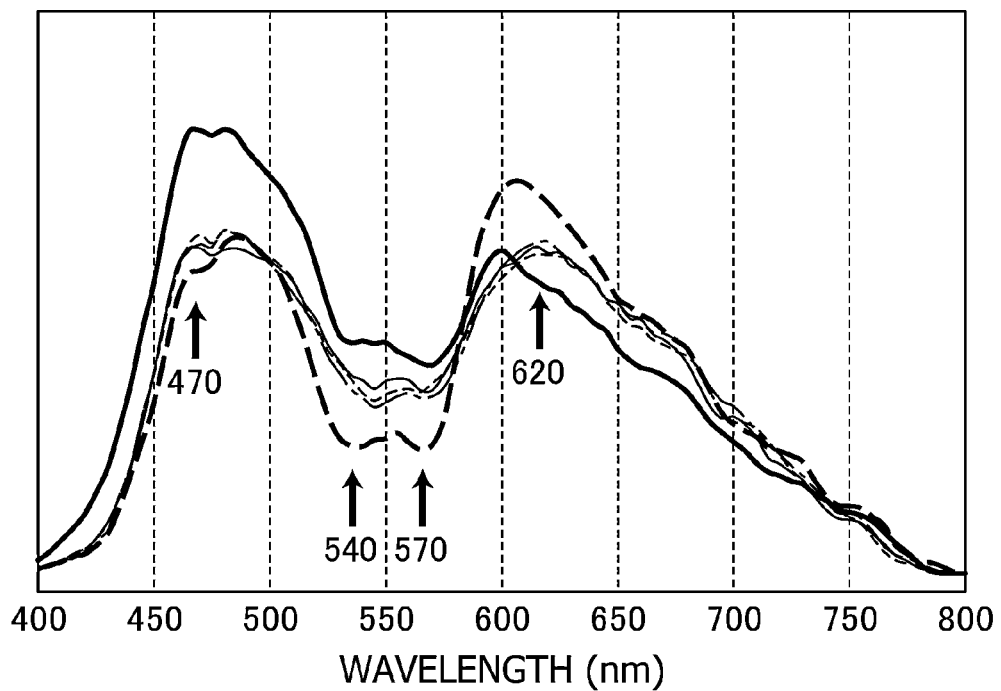
FIGS. 2A and 2B are graphs showing spectral image data of a gastric mucosa obtained by the diagnostic system according to the embodiment.
Figure 2B:
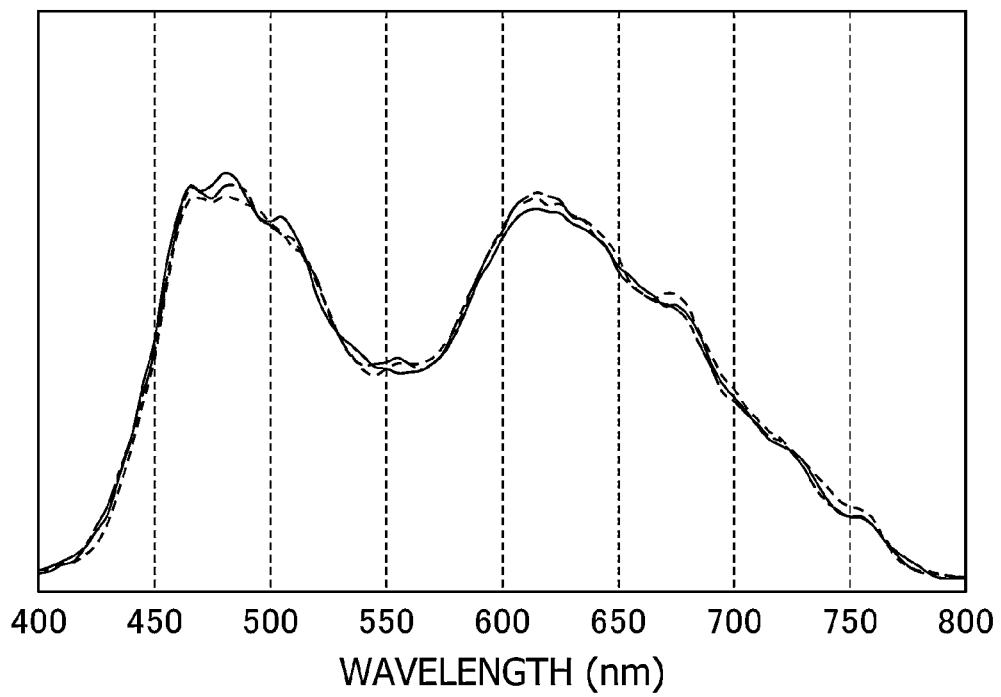

First, a fundamental principle for discriminating between a diseased portion and a healthy portion and an index-value based on which the indicator image is generated by the image processing unit 500 are explained. FIG. 2 shows graphs of spectral representation (i.e., representation of the intensity distribution with respect to the wavelength) of the spectral image data of a gastric mucosa obtained by the diagnostic system 1 according to the embodiment. Each waveform represents a spectrum of a particular pixel in a spectral image obtained by the image pick-up device 141. FIG. 2A represents a spectrum of a pixel corresponding to a diseased portion of the gastric mucosa, and FIG. 2B represents a spectrum of a pixel corresponding to a healthy portion of the gastric mucosa. It should be noted that a predetermined standardization process is applied to the spectrum of each pixel of the healthy portion and the diseased portion shown in FIGS. 2A and 2B. Specifically, since each pixel of the image pickup device 141 receives different amount of light depending on angle differences between the subject (living tissue T) and the illumination light emitted from the tip portion 131a of the light guide 131 and distance differences between the insertion tube tip portion 111 (FIG. 1) and the living tissue T (i.e., the image pick-up device 141 is not able to receive a constant light amount over the entire light-receiving surface thereof), influences of these light amount differences are corrected. It has been proved from experiments that the spectrum of a pixel corresponding to a healthy portion and the spectrum of a pixel corresponding to a diseased portion show similar properties particularly on a higher wavelength side (i.e., they have almost no difference). Therefore, in this embodiment, for each of spectrums of pixels, the intensity values of a predetermined wavelength band (e.g., the wavelength of 600 nm to 800 nm) are integrated, and the size of the entire spectrum (the intensity value at each wavelength) is corrected so that the integrated value becomes a predetermined reference value. That is, in this embodiment, by making the spectrums of the pixels uniform to match a reference size through the standardization process, a spectrum of a pixel corresponding to a diseased portion can be precisely compared with a spectrum of a pixel corresponding to a healthy portion.

As shown in FIG. 2, the spectrums of the gastric mucosa image are similar in that, regardless whether it is a healthy portion or a diseased portion, the spectrum exhibits a substantially M-shaped property having a valley (bottom) in a wavelength region of 500 nm to 590 nm, but are different in that the dispersion of the spectrums of the pixels corresponding to the diseased portion is larger than the dispersion of the spectrums of the pixels corresponding to the healthy portion, and the spectrum of the pixel corresponding to the diseased portion has two bottoms at the wavelengths of approximately 540 nm and approximately 570 nm. It is considered that these differences are caused by the fact that, as known in the field of pathology, a diseased portion and a healthy portion have different component ratios of oxyhemoglobin and deoxyhemoglobin, and the light absorption property is different between oxyhemoglobin and deoxyhemoglobin. The present invention was made by focusing on the above described points, and as described later, the inventor of the present invention invented the technique for quantitatively obtaining the component ratio of oxyhemoglobin and deoxyhemoglobin based on the difference in light absorption property between oxyhemoglobin and deoxyhemoglobin, and, by enhancing this technique, invented a configuration for quantitatively judging the healthy portion and the diseased portion.

Figure 3:
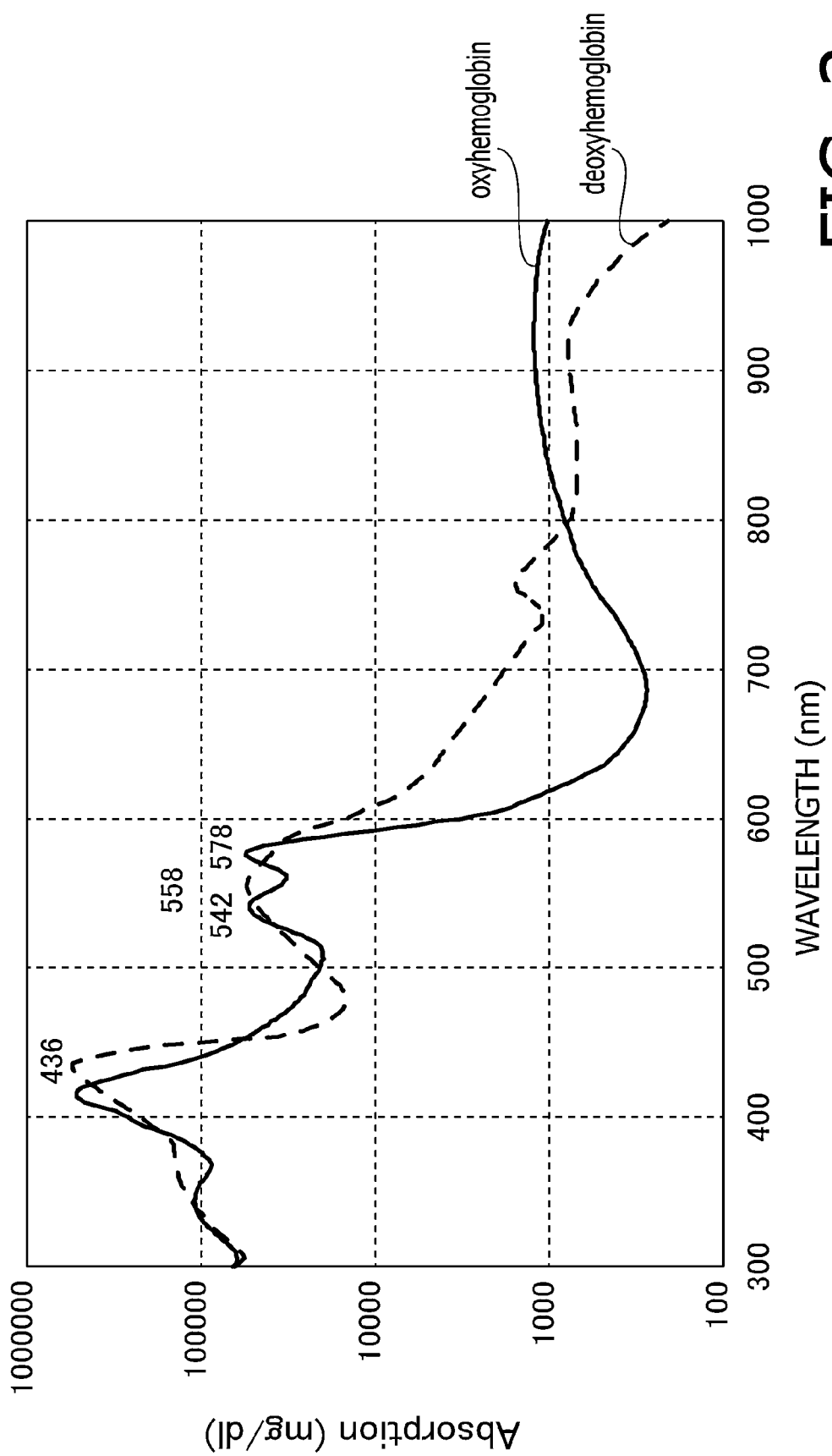
FIG. 3 is a graph showing an absorption property of hemoglobin.

FIG. 3 is a graph representing light absorption properties of hemoglobin. A solid line represents a light absorption property of oxyhernoglobin, and a dashed line represents a light absorption property of deoxyhemoglobin. In FIG. 3, the vertical axis represents the absorption (unit: mg/dl) in spectroscopy and the horizontal axis represents the wavelength (unit: nm). As shown in FIG. 3, oxyhemoglobin and deoxyhemoglobin are common in that they absorb light with the wavelength of 500 nm to 590 nm (i.e., the absorption property increases in the wavelength range of 500 nm to 590 nm), but differ in that the property of deoxyhemoglobin has one peak at the wavelength of approximately 558 nm, whereas the property of oxyhemoglobin has two peaks at the wavelengths of approximately 542 nm and approximately 578 nm and has a bottom at the wavelength of approximately 560 nm. The absorption of oxyhemoglobin is higher at the wavelengths of approximately 542 nm and approximately 578 nm than the absorption of deoxyhemoglobin, and is lower at the wavelength of approximately 558 nm than the absorption of deoxyhemoglobin.

In general, a measurement model of the absorption property of hemogrobin shown in FIG. 3 is expressed as the following expression (3) based on Beer-Lambert Law.

$$A(\lambda) = -\log_{10}\frac{I(\lambda)}{I_0(\lambda)} = \varepsilon(\lambda)Cd \qquad \text{(EXPRESSION 3)}$$

In the expression (3), A is an absorption of a medium (living tissue T), $I_0$ is an emission intensity of light before entering a medium (intensity of incident light), I is an intensity of light traveled in the medium for a distance of d (emission intensity of light), $\varepsilon$ is a molar light absorption coefficient, C is a mol concentration, and $\lambda$ is a wavelength of light. If the medium has n types of light-absorbing substances, then the absorption is expressed as the following expression (4).

$$A(\lambda) = \sum_{i}^{n} \varepsilon_i(\lambda)C_i d \qquad \text{(EXPRESSION 4)}$$

That is, when the medium has n types of light-absorbing substances, the absorption is expressed as the sum total of the absorption properties of the light-absorbing substances. That is, in this embodiment, since the living tissue T is considered to have two light-absorbing substances including oxyhemoglobin and deoxyhemoglobin, the absorption of the living tissue T can be regarded as the sum of absorption properties of oxyhemoglobin and deoxyhemoglobin.

The spectral image data in this embodiment is obtained by receiving, on the image pick-up device 141, reflected light produced when the light emitted from the tip portion 131a of the light guide 131 is reflected from the living tissue T. That is, it means that light not absorbed by oxyhemoglobin and deoxyhemoglobin constituting the living tissue T is observed as the reflected light. It has been reported that, in such a measurement model, information regarding the reflected light from the living tissue T can be processed as a pseudo-transmissive spectrum. That is, the spectral image data according to the embodiment can be regarded as the transmitted light regarding the absorbing substances (i.e., the emission intensity of light I of the above described expressions 3 and 4) in the above described measurement model. Therefore, it is possible to obtain, from the spectral image data of the embodiment, the absorption of the living tissue T by the expressions 3 and 4.

Figure 4:
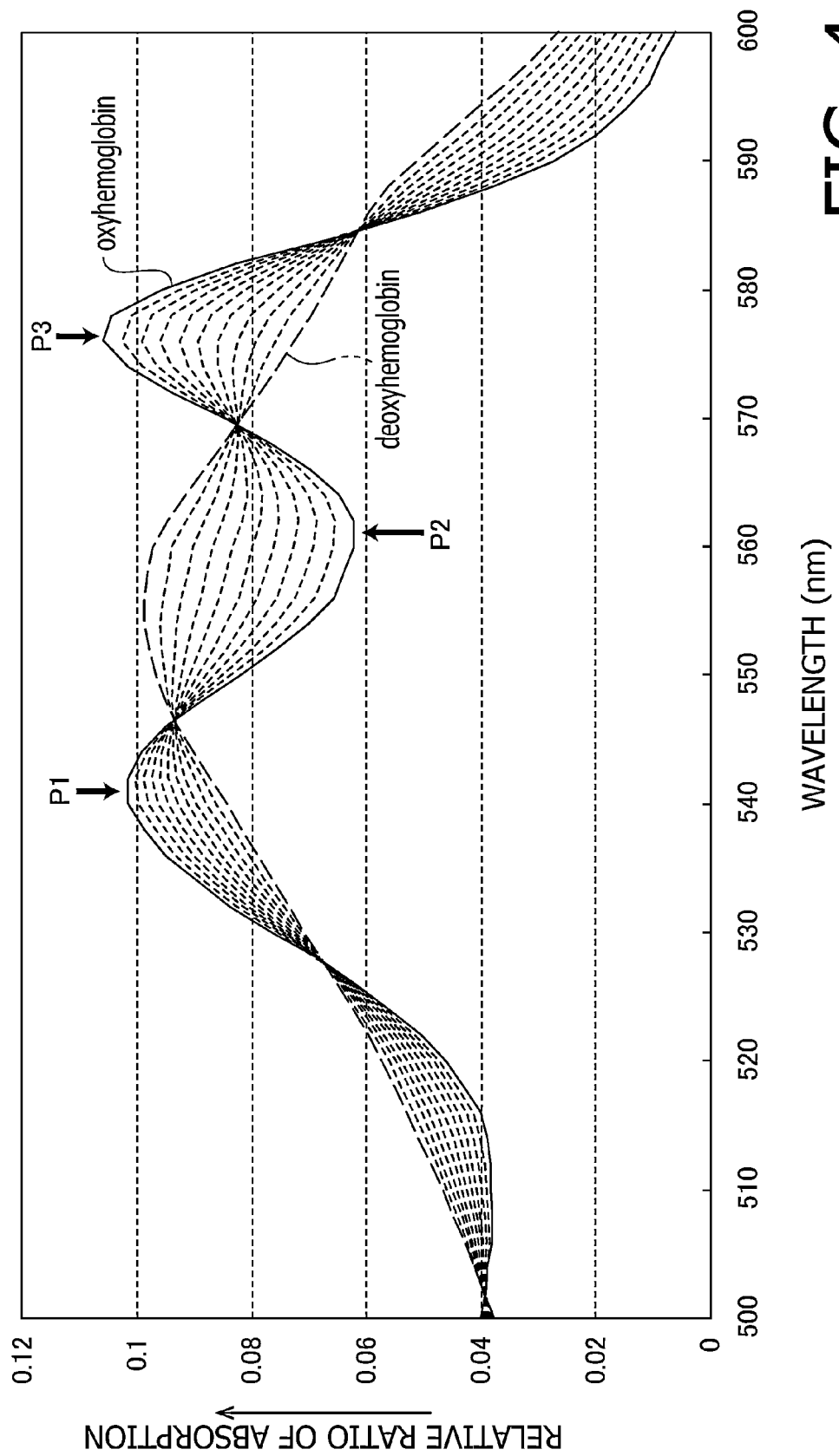
FIG. 4 is a graph enlarging an absorption property of hemoglobin shown in FIG. 3 in the range of wavelength of 520 nm to 600 nm.

FIG. 4 is a graph enlarging the absorption property of hemoglobin shown in FIG. 3 in the range of wavelength of 500 nm to 600 nm. For convenience of explanation, the vertical axis is represented as the relative ratio of the absorption.

As described above, deoxyhemoglobin has the highest absorption at the wavelength of approximately 558 nm, and the absorption property of oxyhemoglobin has two peaks at the wavelengths of approximately 542 nm and approximately 578 nm, and has the bottom at the wavelength of approximately 558 nm. The absorption of oxyhemoglobin is higher at the wavelengths of approximate 542 nm and approximately 578 nm than the absorption of deoxyhemoglobin, and is lower at the wavelength of approximately 558 nm than the absorption of deoxyhemoglobin.

Since as described above the absorption of the living tissue T can be represented as the sum of the absorption properties of oxyhemoglobin and deoxyhemoglobin, the absorption of the living tissue T can be represented as the superposition of the two absorption properties depending on the component ratio of oxyhemoglobin and deoxyhemoglobin in the living tissue T. That is, as shown by dotted lines in FIG. 4, the absorption of the living tissue T is represented as a curve passing through an intermediate portion between the absorption property of oxyhemoglobin represented by a solid line and the absorption property of deoxyhemoglobin represented as a dashed line. Accordingly, it is possible to obtain the component ratio of oxyhemoglobin and deoxyhemoglobin from the absorption. In FIG. 4, the dotted lines are formed by plotting the ratio of the absorption while changing the ratio between oxyhemoglobin and deoxyhemoglobin, at intervals of 10%, within the range from 10%:90% to 90%:10%.

As described above, by obtaining the absorption from the spectral image data of each pixel obtained by the image processing unit 500 using the expressions 3 and 4, it is possible to quantitatively obtain the ratio between oxyhemoglobin and deoxyhemoglobin. Specifically, a concentration index α of oxyhemoglobin is obtained by obtaining the intensity values (spectral image data) at the wavelengths of 542 nm (hereafter, referred to as a "characterizing point P1"), 558 nm (hereafter, referred to as a "characterizing point P2"), 578 nm (hereafter, referred to as a "characterizing point P3"), by converting them into absorptions using the expressions 3 and 4, and by assigning the absorptions to the following expression 5.

$$\alpha = (A_2-A_1)+(A_2-A_3)=2A_2-A_1-A_3 \qquad \text{(EXPRESSION 5)}$$

where $A_1$ to $A_3$ are absorptions at the characterizing points P1 to P3, respectively. According to this expression, the concentration index α of oxyhemoglobin becomes smaller (becomes negatively larger), as the spectral image data at the characterizing points P1 to P3 gets closer to the absorption property of oxyhemoglobin. The concentration index α of oxyhemoglobin becomes larger, as the spectral image data at the characterizing points P1 to P3 gets closer to the absorption property of deoxyhemoglobin (i.e., as the ratio of deoxyhemoglobin gets higher). That is, it can be said that the concentration index α of oxyhemoglobin is an index-value representing the concentration of oxyhemoglobin contained in the spectral image data. Therefore, when the light-absorbing substances of the living tissue T are the two types of substances, i.e., oxyhemoglobin and deoxyhemoglobin, the concentration index α of oxyhemoglobin is an index-value representing the ratio between oxyhemoglobin and deoxyhemoglobin.

As described above, by utilizing the relationship between the spectrum of the spectral image and the absorption properties of oxyhemoglobin and deoxyhemoglobin, it is possible to precisely obtain the ratio between oxyhemoglobin and deoxyhemoglobin contained in the living tissue T. However, in this technique, it is required to convert the spectral image data into the absorption and to execute the logarithmic calculation and the concentration conversion for each of the pixels constituting the spectral image, which causes a heavy load as a real time process. The inventor of the present invention focused on the fact that a spectrum of a spectral image obtained according to the embodiment can be regarded as transmitted light of light-absorbing substances (i.e., oxyhemoglobin and deoxyhemoglobin) in the living tissue T, and invented the technique for more easily obtaining the ratio between oxyhemoglobin and deoxyhemoglobin by considering the absorption model of hemoglobin as a transmission type model.

Figure 5:
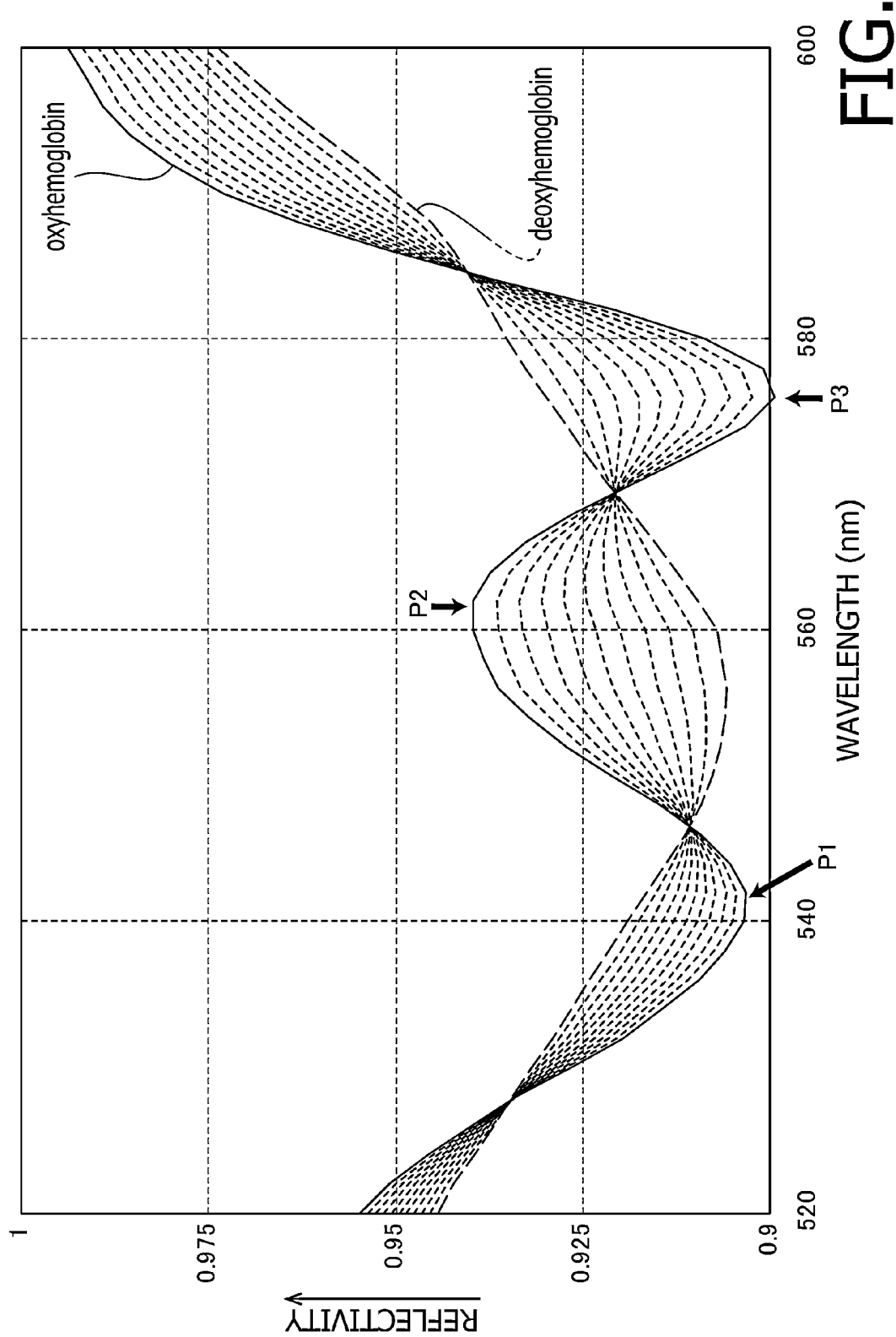
FIG. 5 is a graph illustrating a transmission property of hemoglobin.

FIG. 5 is a graph illustrating a transmission property of hemoglobin. In FIG. 5, the vertical axis represents reflectivity, and the horizontal axis represents wavelength (unit: nm). In FIG. 5, only a range where the reflectivity is larger than or equal to 0.9 is illustrated, and as in the case of FIG. 4, a solid line represents a property of oxyhemoglobin, and a dashed line represents a property of deoxyhemoglobin. In FIG. 5, dotted lines are formed by plotting the reflectivity while changing the ratio between oxyhemoglobin and deoxyhemoglobin, at intervals of 10%, within the range from 10%:90% to 90%:10%.

As shown in FIG. 5, the transmission property of hemoglobin has a property reversed in the up and down direction from the absorption property of hemoglobin shown in FIG. 4. That is, the reflectivity of deoxyhemoglobin becomes the lowest at the wavelength of approximately 558 nm, and the reflectivity of oxyhemoglobin has two bottoms at the wavelengths of approximately 542 nm and approximately 578 nm and has a peak at the wavelength of approximately 558 nm. The reflectivity of oxyhemoglobin becomes lower than the reflectivity of deoxyhemoglobin at the wavelengths of approximately 542 nm and approximately 578 nm and becomes higher than the reflectivity of deoxyhemoglobin at the wavelength of approximately 558 nm.

Since the spectrum of the spectral image obtained according to the embodiment can be regarded as the transmitted light regarding the light-absorption substances (i.e., oxyhemoglobin and deoxyhemoglobin) in the living tissue T, it can be said that a spectrum of a spectral image itself is information concerning the transmissivity (in other words, the reflectivity). Therefore, in this embodiment, a concentration index β of oxyhemoglobin is obtained by obtaining the intensity values at the characterizing points P1 to P3 for the spectral image data of each pixel obtained by the image processing unit 500 and by assigning the intensity values to the following expression 6.

$$\beta = (P_2 - P_1) + (P_2 - P_3) = 2P_2 - P_1 - P_3 \quad \text{(EXPRESSION 6)}$$

where $P_1$ to $P_3$ are the intensity values of the characterizing points P1 to P3. According to the expression 6, as the spectral image data at the characterizing pints P1 to P3 gets closer to the absorption property of oxyhemoglobin (i.e., as the ratio of oxyhemoglobin gets higher), the concentration index β of oxyhemoglobin becomes large. As the spectral image data at the characterizing pints P1 to P3 gets closer to the absorption property of deoxyhemoglobin (i.e., as the ratio of deoxyhemoglobin gets higher), the concentration index β of oxyhemoglobin becomes small (the concentration index β of oxyhemoglobin becomes negatively large). That is, as in the case if the concentration index α of oxyhemoglobin of the absorption type model, the concentration index β of oxyhemoglobin is the index-value representing the ratio between oxyhemoglobin and deoxyhemoglobin. Since, in contrast to the concentration index α of oxyhemoglobin of the absorption type model, the concentration index β of oxyhemoglobin does not require the logarithmic calculation (i.e., the concentration index β can be obtained only by the addition and subtraction calculation), the calculation load is low, which is adapted for real time processing.

Figure 6:
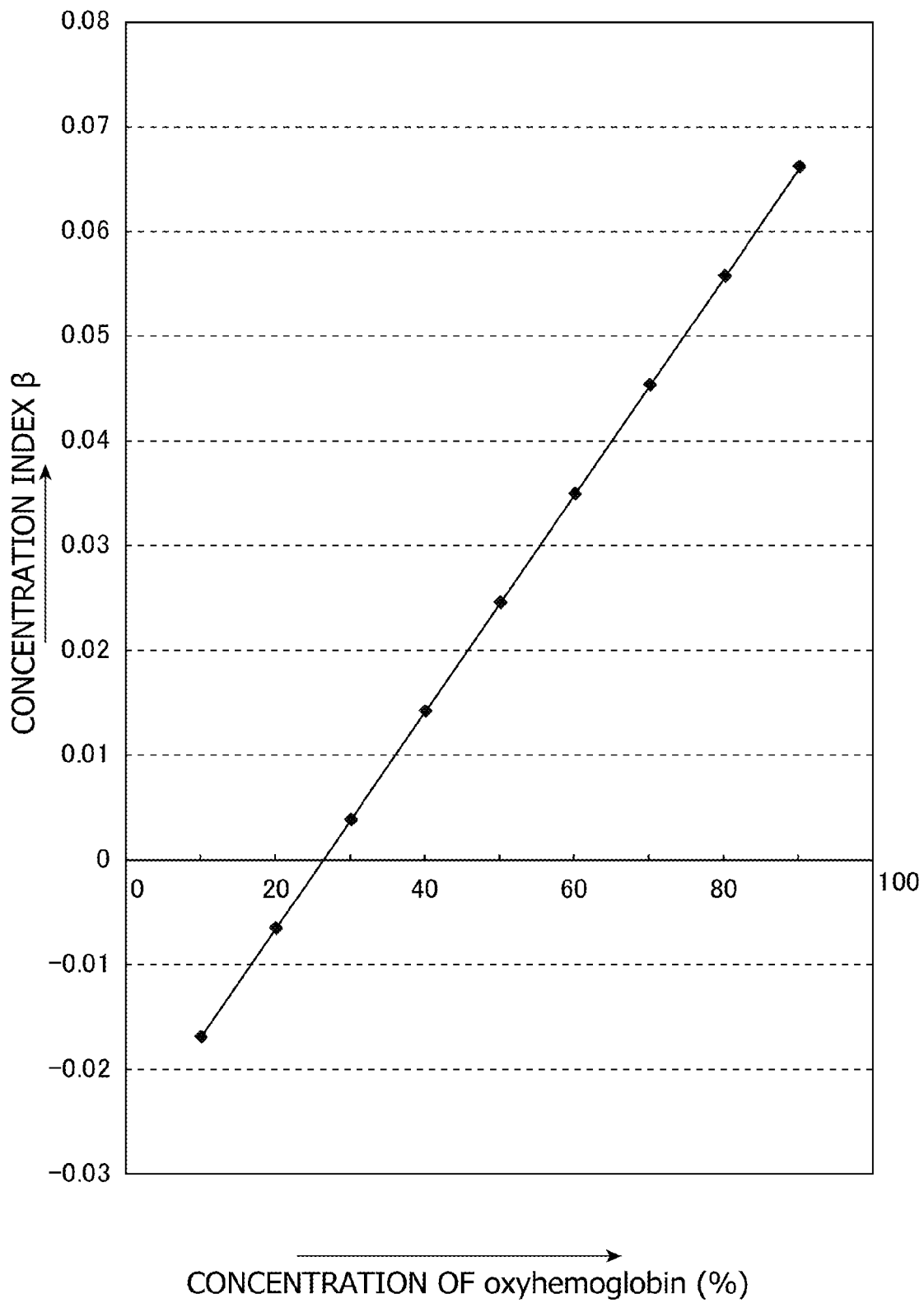
FIG. 6 is a graph illustrating a relationship between a concentration index β and concentration of oxyhemoglobin.

If the concentration index β of oxyhemoglobin (i.e., the index-value) is obtained, the ratio between oxyhemoglobin and deoxyhemoglobin can be obtained. FIG. 6 is a graph illustrating the relationship between the concentration index β and the concentration of oxyhemoglobin. FIG. 6 shows the concentration index β of oxyhemoglobin obtained by changing the ratio between oxyhemoglobin and deoxyhemoglobin, at intervals of 10%, within the range from 10%:90% to 90%:10%.

As shown in FIG. 6, the concentration index β and the concentration (ratio) of oxyhemoglobin can be approximated in a linear relationship in the range of the reflectivity of approximately 0.90 to 0.94, and therefore the ratio of oxyhemoglobin can be uniquely obtained when the concentration index β is determined. That is, it is understood that, academically the measurement model complies with the Beer-Lambert Law, but, in an extremely small range, the approximation can be obtained by calculation of the transmissivity. In this embodiment, by using such a relationship between the concentration index β and the concentration (ratio) of oxyhemoglobin, the concentration index β is assigned to the expression of the linear line of FIG. 6, and the component ratio of oxyhemoglobin and deoxyhemoglobin of the living tissue T is obtained.

As described above, in this embodiment, the concentration index β of oxyhemoglobin is obtained for the spectral image data of each pixel, and the ratio of oxyhemoglobin is obtained from the concentration index β. The sequence of these calculation is be achieved merely by the four arithmetic operations. Therefore, according to the configuration of the embodiment, the processing load can be considerably reduced in comparison with the above described absorption model. The image processing unit 500 according to the embodiment generates an indicator image based on the ratio of oxyhemoglobin uniquely determined from the concentration index β (index-value).

Figure 7:
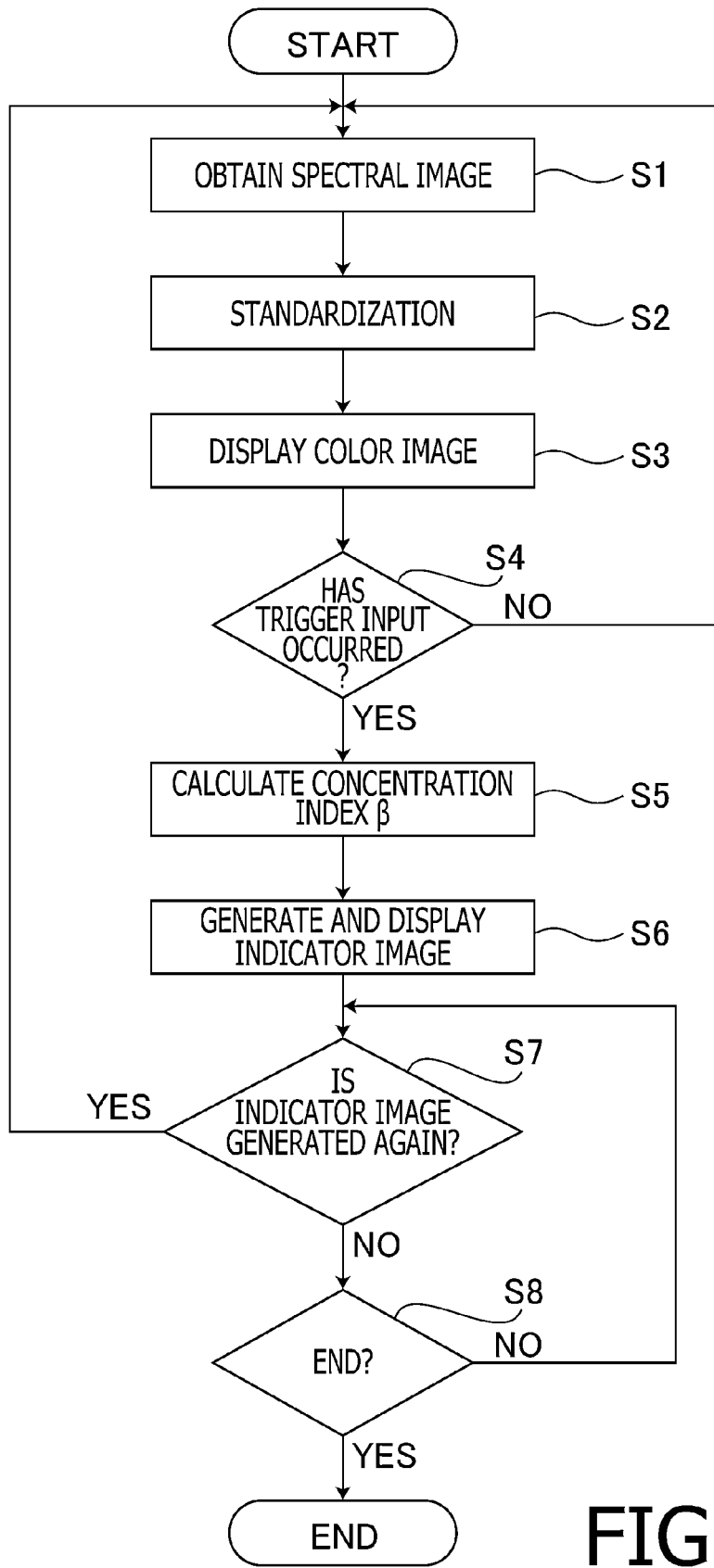
FIG. 7 is a flowchart illustrating an image generation process executed by an image processing unit of the diagnostic system according to the embodiment of the invention.
Figure 8A:
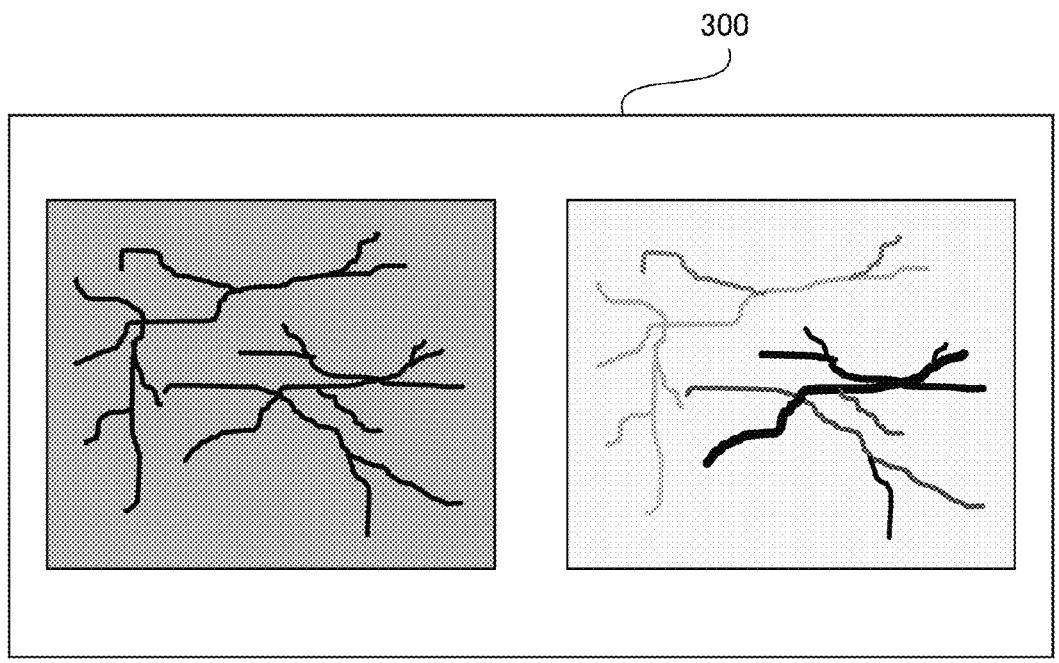
FIGS. 8A and 8B schematically illustrate a color image and an indicator image displayed on an image display device through the image generation process shown in FIG. 7.
Figure 8B:
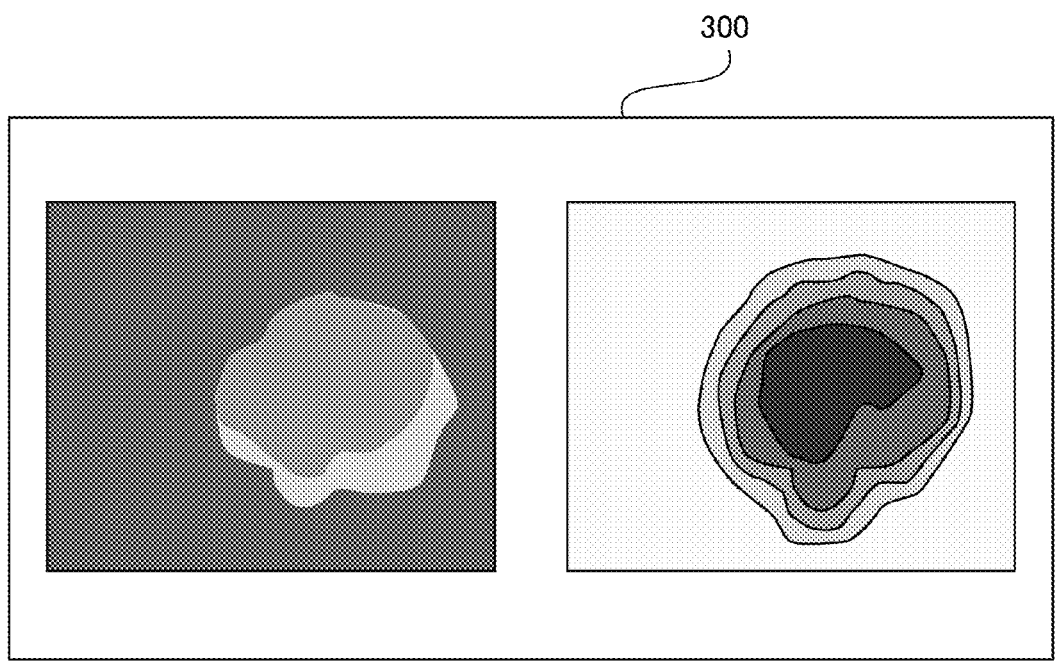

Hereafter, an image generation process executed by the image processing unit 500 according to the embodiment is explained. FIG. 7 is a flowchart illustrating the image generation process executed by the image processing unit 500 according to the embodiment. FIG. 8 schematically illustrates a color image and an indicator image displayed on the image display device 300 through the image generation process shown in FIG. 7. FIG. 8A is a schematic illustration of an image obtained when blood vessels of the living tissue T are observed from a relatively distant position, and FIG. 8B is a schematic illustration of an image obtained when a tumor (capillary blood vessels) of the living tissue T is observed from a relatively near position. The image generation process is a routine for generating a color image and an indicator image and displaying these images on the image display device 300. The routine is executed in response to power-on of the diagnostic system 1.

When the routine is started, step S1 is processed. In step S1, the image processing unit 500 transmits a control signal to the filter control unit 420 to obtain a spectral image. When the control signal is received, the filter control unit 420 controls the rotation angle of the spectral filter 410 to sequentially select the wavelength of light having narrow bands (a band width of approximately 5 nm) of 400, 405, 410, . . . 800 nm. The image processing unit 500 shoots the spectral image obtained at each wavelength and stores it in the temporary memory 520 as the spectral image data. Then, the process proceeds to step S2.

In step S2, a spectrum is obtained for each pixel of the spectral image obtained in step S1, and standardization is executed for the spectrum of each pixel. Specifically, the intensity values of each pixel in a predetermined wavelength region (e.g., 600 nm to 800 nm) are integrated, and a gain is obtained such that the integrated value becomes a predetermined reference value. Then, the entire spectrum (i.e., the intensity values at each wavelength) is multiplied by the gain, and fluctuations of the spectrum of each pixel are corrected (i.e., the spectral image data of each pixel is standardized). Then, the process proceeds to step S3.

In step S3, spectral image data obtained from three spectral images having the center wavelengths of 435 nm, 545 nm and 700 nm is extracted from the spectral image data standardized in step S2, and a piece of color image data is generated by assigning the spectral image data having the center wavelength of 435 nm to a blue plane, assigning the spectral image data having the center wavelength of 545 nm to a green plane and assigning the spectral image data having the center wavelength of 700 nm to a red plane. As described above, this color image data is obtained from the spectral image at the wavelength of 435 nm corresponding to blue, the spectral image at the wavelength of 545 nm corresponding to green and the spectral image at the wavelength of 700 nm corresponding to red, and is a color image equivalent to an normal endoscopic image. Then, the image processing unit 500 transmits the generated color image data to the video memory 540 to display it in the left side on the screen of the image display device 300 (FIGS. 8A and 8B). Then, the process proceeds to step S4.

In step S4, it is judged whether an operation unit (not shown) of the processor 200 for an electronic endoscope is operated and thereby a trigger input instructing generation of an indicator image occurs while the steps S1 to S3 are processed. When no trigger input occurs (S4: NO), the process returns to S1 to obtain the spectral image again. That is, unless a trigger input occurs, the color image obtained from the spectral image continues to be displayed on the image display device 300 in a sequential updating manner. On the other hand, when a trigger input has occurred during execution of steps S1 to S3 (S4: YES), the process proceeds to step S5.

In step S5, calculation of the concentration index α of oxyhemoglobin is executed from the spectral image data standardized in step S2. Specifically, for all the pixels of the spectral image, the spectral image data corresponding to the characterizing points P1 to P3, i.e., the spectral image data at the wavelength of 540 nm (≅542 nm) corresponding to the characterizing point P1, the spectral image data at the wavelength of 560 nm (≅558 nm) corresponding to the characterizing point P2 and the spectral image data at the wavelength of 580 nm (≅578 nm) corresponding to the characterizing point P3, are assigned to the expression 6 to obtain the concentration index β of oxyhemoglobin. Then, the process proceeds to step S6.

In step S6, based on the concentration index β of oxyhemoglobin obtained in step S5, the indicator image is generated. Specifically, the concentration of oxyhemoglobin is obtained from the concentration index β of oxyhemoglobin of each pixel of the spectral image (i.e., the index-value) and the expression of the linear line of the graph shown in FIG. 6, and a certain color corresponding to the obtained concentration is assigned to each pixel to generate the indicator image. In this embodiment, a so-called color gradation image, in which color changes in a sequence of purple, blue, green, yellow and red depending on the concentration of oxyhemoglobin, is generated as the indicator image. Then, the image processing unit 500 sends the data of the generated indicator image to the video memory 540 to display the indicator image on the right side on the screen of the image display device 300 (FIGS. 8A and 8B). By thus arranging, on the screen of the image display device 300, the indicator image color-coded depending on the concentration of oxyhemoglobin and the color image of the endoscopic image, the user of the diagnostic system 1 is able to judge which region in the color image is a diseased portion by comparing the color image with the indicator image. Then, the process proceeds to step S7.

In step S7, the image processing unit 500 displays, on the image display device 300, a message inquiring about whether to generate again the indicator image, and accepts an input from the operation unit (not shown) of the processor 200 for an electronic endoscope. When the user of the diagnostic system 1 operates the operation unit and selects re-generating of the indicator image (S7: YES), the process returns to step S1. On the other hand, no instruction for re-generating of the indicator image is inputted for a predetermined time period (e.g., several seconds) (S7: NO), the process proceeds to step S8.

In step S8, the image processing unit 500 displays, on the image display device 300, a message inquiring about whether to terminate displaying of the indicator image, and accepts an input from the operation unit (not shown) of the processor 200 for an electronic endoscope. When the user of the diagnostic system 1 operates the operation unit and selects terminating of the indicator image (S8: YES), the process terminates. On the other hand, no instruction for displaying of the indicator image is inputted for a predetermined time period (e.g., several seconds) (S7: NO), the process proceeds to step S7.

As described above, through execution of the routine shown as the flowchart in FIG. 7 by the image processing unit 500, the indicator image which can be advantageously used for assuming a position of the diseased portion is displayed on the image display device 300. By thus displaying a region which is highly likely a diseased portion as an indicator image, a medical doctor is able to make a diagnosis while identifying a position and a range of a diseased portion and making a comparison with a peripheral tissue.

As described above, in this embodiment, by obtaining, for the spectral image data of each pixel, the concentration index β of oxyhemoglobin while assigning the spectral image data corresponding to the characterizing points P1 to P3 (i.e., the intensity values at the wavelengths of 540 nm (≅542 nm), 560 nm (≅558 nm) and 580 nm (≅578 nm)) to the expression 6, a region (pixel) which is highly likely to be a diseased portion is identified from the concentration of oxyhemoglobin (i.e., the ratio between oxyhemoglobin and deoxyhemoglobin) defined from the concentration index β of oxyhemoglobin. That is, by only executing simple four arithmetic operations using three spectral image data of each pixel, a region (pixel) which is highly likely a diseased portion can be identified. Since the process for generating and displaying the indicator image can be performed at a high speed, it becomes possible to provide the indicator image without causing a time lag, while displaying a color image in real time.

The foregoing is the explanation about the embodiment of the invention; however, the invention is not limited to the above described embodiment, and can be varied within the technical scope of the invention. For example, in the above described embodiment, the concentration index β of oxyhemoglobin is obtained by applying the expression 6 to the standardized spectral image data; however, the invention is not limited to such a configuration. For example, a concentration index γ of oxyhemoglobin may be obtained by the following expression 7, for the spectral image data of each pixel before standardization.

$$\gamma = \frac{2P_2 - P_1 - P_3}{a} \quad \text{(EXPRESSION 7)}$$

$$a = \sum Ii$$

where Ii represents an intensity value of the spectral image data at each wavelength, and "a" represents an integrated value of spectral waveforms of respective pixels. Since the integrated value a of the spectrum waveforms of the respective pixels can be regarded as a parameter (a standardization coefficient) indicating the amount of light incident on each pixel, the effect by a difference in light amount between the pixels can be corrected and the standardization can be achieved by obtaining the concentration index γ of oxyhemoglobin. That is, by obtaining the spectral image data $P_1$, $P_2$ and $P_3$ corresponding to the characterizing points P1 to P3 for the spectral image data of each pixel before standardization, by obtaining the integrated value a of all the spectral image data, and by assigning them to the expression 7, the standardization can be achieved mathematically. As a result, it becomes possible to include a process corresponding to step S2 of the above described embodiment. Although, in this variation, the spectral image data obtained for all the wavelengths is integrated to obtain the standardization coefficient, the spectral image data in a predetermined wavelength region (e.g., the wavelength of 600 nm to 800 nm) may be integrated as the standardization coefficient as in the case of the above described embodiment.

In the standardization process according to the embodiment, the intensity values in a predetermined wavelength region (e.g. the wavelength of 600 nm to 800 nm) are integrated for the spectrum of each pixel of the spectral image, and the size of the entire spectrum (i.e., the intensity value at each wavelength) is corrected so that the integrated value becomes the predetermined reference value; however, the invention is not limited to such a configuration. For example, the process may be configured such that a predetermined wavelength range can be selected from the range of 600 nm to 800 nm, the intensity values in the selected wavelength range are integrated, and the size of the entire spectrum is corrected so that the integrated value becomes the predetermined reference value.

It is known that, at an isosbestic point of hemoglobin, the absorption property of oxyhemoglobin and the absorption property of deoxyhemoglobin necessarily intersect with each other. Therefore, the size of the spectrum may be corrected so that the spectral image data (intensity value) at the wavelength corresponding to the isosbestic point of hemoglobin becomes a predetermined reference value. Specifically, when the spectral image data at the wavelength (528 nm) corresponding to the isosbestic point of hemoglobin is defined as Q1, the spectral image data at the wavelength (585 nm) corresponding to the isosbestic point of hemoglobin is defined as Q2, and the spectral image data at the wavelength (560 nm) corresponding to the isosbestic point of hemoglobin is defined as Q3, by obtaining the concentration index γ of oxyhemoglobin by the following expression 8, the effect of a difference in light amount between the pixels is corrected and the standardization is achieved.

$$\gamma = \frac{(Q_1 - P_1) - \left(\frac{Q_1 - Q_3}{2} - P_2\right) + (Q_3 - P_3) - \left(\frac{Q_1 - Q_3}{2} - P_2\right)}{a}$$ (EXPRESSION 8)

Since the concentration (ratio) and the concentration index γ of oxyhemoglobin and the concentration (ratio) and the concentration index γ of deoxyhemoglobin are also approximated linearly, the ratio of oxyhemoglobin can be uniquely defined by obtaining the concentration index γ. When the isosbestic point is utilized, it becomes possible to measure the total amount of hemoglobin with a stable accuracy because oxyhemoglobin and deoxyhemoglobin have the same absorption. The total amount of hemoglobin is an amount which is proportional to the concentration index γ obtained by the following expressions 9 and 10.

$$\gamma = \frac{Q_3}{a}$$ (EXPRESSION 9)

$$\gamma = \frac{Q_1}{a}$$ (EXPRESSION 10)

As long as the spectrum of the pixel corresponding to the diseased portion can be discriminated from the spectrum of the pixel corresponding to the healthy portion, it is not necessarily required to obtain the spectral image data at the intervals of 5 nm. The wavelength interval at which the spectral image data is obtained may be selectable, for example, in the range of 1 nm to 10 nm. Therefore, by obtaining the spectral image at smaller wavelength intervals, it becomes possible to obtain more precisely the spectral image data corresponding to the characterizing points P1 to P3.

In this embodiment, the image processing unit 500 is configured to generate the indicator image by assigning predetermined colors corresponding to the respective concentrations of oxyhemoglobin to the pixels of the spectral image; however, the invention is not limited to such a configuration. For example, the indicator image may be displayed in a gray scale representation depending on the concentration of oxyhemoglobin.

In the image generation process according to the embodiment, the concentration index β of oxyhemoglobin of each pixel of the spectral image is obtained and the concentration of oxyhemoglobin is obtained from the expression of the linear line of the graph shown in FIG. 6, and the indicator image is generated by assigning a predetermined color corresponding to the concentration to each pixel (step S6); however, the invention is not limited to such a configuration. As described above, the concentration (ratio) of oxyhemoglobin and the concentration index β of oxyhemoglobin are in a linear relationship. Therefore, it is possible to generate the indicator image by assigning, to each pixel, the predetermined color corresponding to the concentration index β of oxyhemoglobin of each pixel of the spectral image, without obtaining the concentration of oxyhemoglobin from the expression of the linear line of the graph shown in FIG. 6.

In the image generation process according to the embodiment, the intensity values at the wavelengths of 540 nm (around 542 nm), 560 nm (around 558 nm) and 580 nm (around 578 nm)) are used as the spectral image data corresponding to the characterizing points P1 to P3, and the concentration index β of oxyhemoglobin is obtained by assigning the intensity values to the expression 6 (step S5); however, the invention is not limited to such a configuration. As described above, the invention utilizes the high/low relationship (a difference in height) of the transmissivity (reflectivity) between oxyhemoglobin and deoxyhemoglobin, where the reflectivity of oxyhemoglobin becomes lower than the reflectivity of deoxyhemoglobin at the wavelengths of approximately 542 nm and approximately 578 nm and becomes higher than the reflectivity of deoxyhemoglobin at the wavelength of approximately 558 nm. Therefore, each of the concentration indexes β and γ of oxyhemoglobin serves as an index-value indicating the ratio between oxyhemoglobin and deoxyhemoglobin in the range where the vertical relationship in transmissivity (reflectivity) between oxyhemoglobin and deoxyhemoglobin is maintained. As a result, as shown in FIG. 5, the intensity value at a certain wavelength in the range of 530 nm to 545 nm can be used as the spectral image data for the characterizing point P1, the intensity value at a certain wavelength in the range of 550 nm to 568 nm can be used as the spectral image data for the characterizing point P2, and the intensity value at a certain wavelength in the range of 570 nm to 584 nm can be used as the spectral image data for the characterizing point P3.

What is claimed is:

1. A diagnostic system, comprising:
a spectral image pickup that picks up a spectral image in a predetermined wavelength region in a body cavity and obtains spectral image data;
an image processor that obtains, from the spectral image data, an index-value for discriminating between a diseased portion and a healthy portion, and generates and outputs an indicator image based on the index-value; and
a monitor on which the indicator image is displayed,
wherein, for each pixel of the spectral image, the image processor defines β obtained by a following expression as the index-value, $$\beta = 2P_2 - P_1 - P_3$$

while using the spectral image data $P_1$ at a first wavelength which is around a wavelength of 542 nm, the spectral image data $P_2$ at a second wavelength which is around a wavelength of 558 nm and the spectral image data $P_3$ at a third wavelength which is around a wavelength of 578 nm.

2. The diagnostic system according to claim 1, wherein the image processor obtains a ratio between oxyhemoglobin and deoxyhemoglobin from the index-value, and generates the indicator image based on the ratio.

3. The diagnostic system according to claim 2, wherein the image processor generates the indicator image by assigning a predetermined color based on the ratio between oxyhemoglobin and deoxyhemoglobin to each pixel of the spectral image.

4. The diagnostic system according to claim 1, wherein:
the image processor outputs a color image by combining the spectral image data in wavelength bands corresponding to blue, green and red; and
the color image and the indicator image are displayed on the monitor while being aligned side by side.

5. The diagnostic system according to claim 1, further comprising a standardizer that integrates the spectral image data in a predetermined wavelength range to obtain an integrated value, and corrects the spectral image data so that the integrated value coincides with a reference value.

6. The diagnostic system according to claim 5, wherein the predetermined wavelength range is selected from a range of 600 nm to 800 nm.

7. The diagnostic system according to claim 1, further comprising a standardizer that corrects the spectral image data so that the spectral image data at a wavelength corresponding to an isosbestic point of hemoglobin coincides with a reference value.

8. The diagnostic system according to claim 1, wherein:
the predetermined wavelength region is 400 nm to 800 nm; and
the spectral image includes a plurality of images shot at an interval of a predetermined wavelength defined in a range of 1 nm to 10 nm.

9. The diagnostic system according to claim 1, wherein:
the first wavelength is a certain wavelength in a range of 530 nm to 545 nm;
the second wavelength is a certain wavelength in a range of 550 nm to 568 nm; and
the third wavelength is a certain wavelength in a range of 570 nm to 584 nm.

10. A diagnostic system, comprising:
a spectral image pickup that picks up a spectral image in a predetermined wavelength region in a body cavity and obtains spectral image data;
an image processor that obtains, from the spectral image data, an index-value for discriminating between a diseased portion and a healthy portion, and generates and outputs an indicator image based on the index-value; and
a monitor on which the indicator image is displayed,
wherein, for each pixel of the spectral image, the image processor defines γ obtained by a following expression as the index-value, $$\gamma = \frac{2P_2 - P_1 - P_3}{a}$$

while using the spectral image data $P_1$ at a first wavelength which is around a wavelength of 542 nm, the spectral image data $P_2$ at a second wavelength which is around a wavelength of 558 nm, the spectral image data $P_3$ at a third wavelength which is around a wavelength of 578 nm and a standardization coefficient indicates an amount of light incident on each pixel.

11. The diagnostic system according to claim 10, wherein the standardization coefficient is an integrated value of the spectral image data at respective wavelengths in the predetermined wavelength region.

12. The diagnostic system according to claim 10, wherein the image processor obtains a ratio between oxyhemoglobin and deoxyhemoglobin from the index-value, and generates the indicator image based on the ratio.

13. The diagnostic system according to claim 12, wherein the image processor generates the indicator image by assigning a predetermined color based on the ratio between oxyhemoglobin and deoxyhemoglobin to each pixel of the spectral image.

14. The diagnostic system according to claim 10, wherein:
the image processor outputs a color image by combining the spectral image data in wavelength bands corresponding to blue, green and red; and
the color image and the indicator image are displayed on the monitor while being aligned side by side.

15. The diagnostic system according to claim 10, wherein:
the predetermined wavelength region is 400 nm to 800 nm; and
the spectral image includes a plurality of images shot at an interval of a predetermined wavelength defined in a range of 1 nm to 10 nm.

16. The diagnostic system according to claim 10, wherein:
the first wavelength is a certain wavelength in a range of 530 nm to 545 nm;
the second wavelength is a certain wavelength in a range of 550 nm to 568 nm; and
the third wavelength is a certain wavelength in a range of 570 nm to 584 nm.

* * * * *